(12) United States Patent
Cinquin et al.

(10) Patent No.: US 9,127,651 B2
(45) Date of Patent: *Sep. 8, 2015

(54) METHOD AND DEVICE FOR CHANGING THE PH OF A SOLUTION

(75) Inventors: Philippe Cinquin, Saint Nazaire les Eymes (FR); François Lenouvel, Grenoble (FR); Vanessa Durrieu, Labege (FR); Stéphane Mathe, Toulouse (FR); Pierre Mozer, Vincennes (FR)

(73) Assignee: UNIVERSITE JOSEPH FOURIER, Toulouse Cedex (FR)

( * ) Notice: Subject to any disclaimer, the term of this patent is extended or adjusted under 35 U.S.C. 154(b) by 1419 days.
This patent is subject to a terminal disclaimer.

(21) Appl. No.: 12/517,395

(22) PCT Filed: Dec. 3, 2007

(86) PCT No.: PCT/FR2007/052435
§ 371 (c)(1),
(2), (4) Date: Jan. 26, 2010

(87) PCT Pub. No.: WO2008/074958
PCT Pub. Date: Jun. 26, 2008

(65) Prior Publication Data
US 2010/0145318 A1    Jun. 10, 2010

(30) Foreign Application Priority Data
Dec. 4, 2006  (FR) ...................................... 06 55296
Dec. 3, 2007  (WO) ................. PCT/FR2007/052435

(51) Int. Cl.
C12M 1/12     (2006.01)
F03G 7/00     (2006.01)
G05D 21/02    (2006.01)
C12M 1/00     (2006.01)

(52) U.S. Cl.
CPC ............... *F03G 7/005* (2013.01); *C12M 25/02* (2013.01); *G05D 21/02* (2013.01); *C12M 29/04* (2013.01)

(58) Field of Classification Search
CPC ...... C12M 29/04; C12M 23/34; C12M 25/02; C12M 23/08; C12M 23/24; C02F 3/1263; B01D 29/0036; B01D 29/0075; B01D 35/12; B01D 29/0047
USPC ...................... 435/297.1; 210/142; 604/891.1
See application file for complete search history.

(56) References Cited

U.S. PATENT DOCUMENTS

| 2005/0158841 | A1* | 7/2005 | Cinquin et al. | 435/252.3 |
| 2005/0170070 | A1* | 8/2005 | Layrolle et al. | 427/2.1 |
| 2006/0011491 | A1* | 1/2006 | Logan et al. | 205/637 |
| 2011/0135967 | A1* | 6/2011 | Pellissier et al. | 429/2 |

FOREIGN PATENT DOCUMENTS

| DE | 04218937 C2 | 7/1995 |
| DE | 19728663 C1 | 10/1998 |
| FR | 2881481 A1 | 8/2006 |
| JP | 1-221169 | 4/1989 |
| WO | 01-16575 A1 | 3/2001 |

OTHER PUBLICATIONS

Translation of the "Written Opinion of the International Searching Authority" issued in PCT/FR2007/052435.
International Search Report from PCT/FR2007/052435 issued on Nov. 3, 2008.

* cited by examiner

*Primary Examiner* — Michael Hobbs
(74) *Attorney, Agent, or Firm* — Vedder Price, P.C.

(57) ABSTRACT

The invention relates to a device (22) for changing the pH of a solvent in which a substance is dissolved. The device includes a housing (24) in contact with the solvent through a housing wall (26) that is permissive to the solvent and the substance. The housing contains enzymes adapted for converting the substance in order to provide hydrogen or hydroxyle ions; the housing wall being non-permissive to the enzymes.

18 Claims, 6 Drawing Sheets

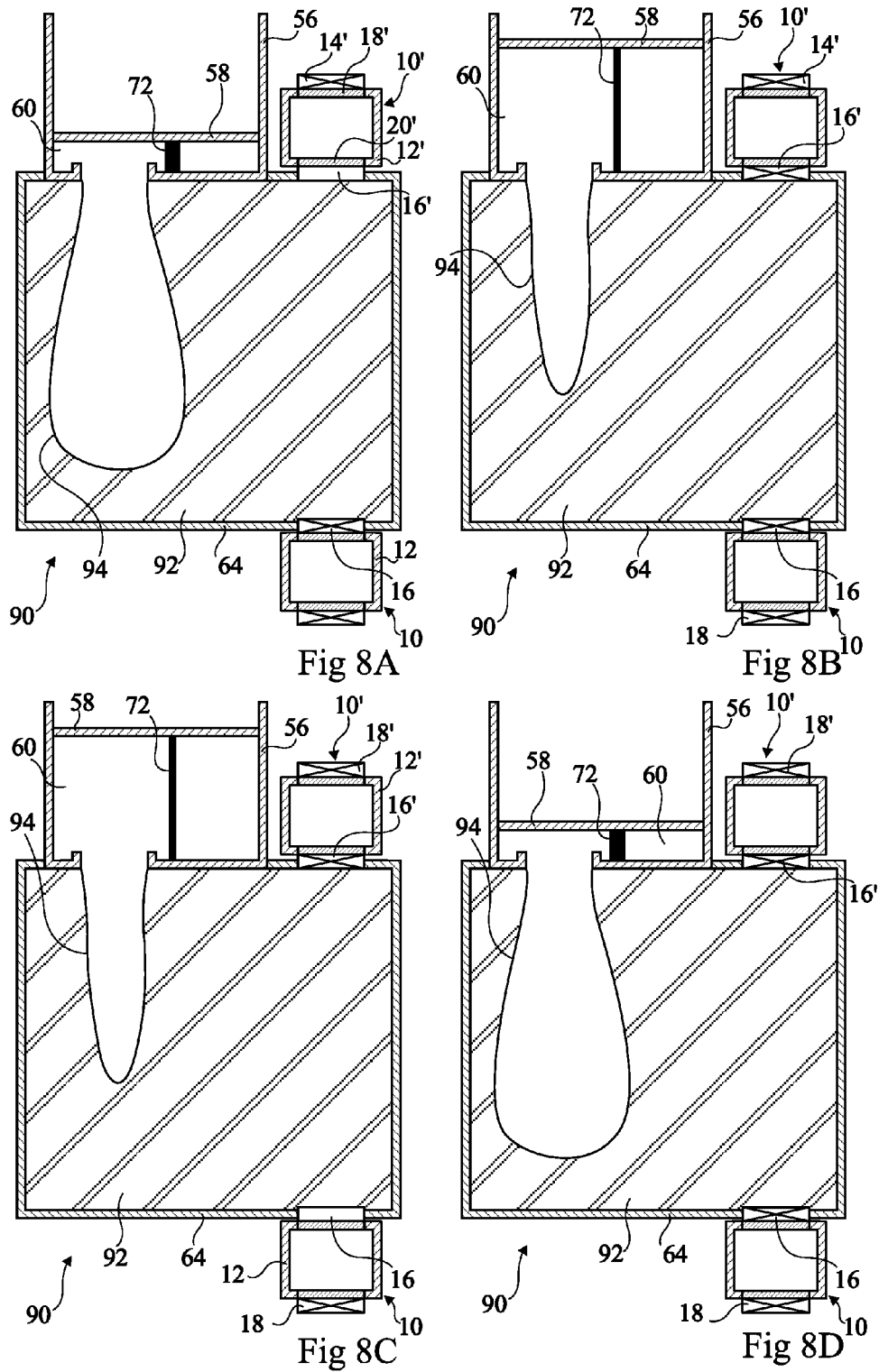

METHOD AND DEVICE FOR CHANGING THE PH OF A SOLUTION

FIELD OF THE INVENTION

The present invention relates to a method and a device for varying the pH of a solution.

DISCUSSION OF PRIOR ART

For certain applications, it is desirable to be able to modify the pH of a solution. An example of application is the regulation of a physico-chemical phenomenon occurring in a solution and having a speed which varies according to the pH of the solution, for example, the variation of the solubilization of a substance in a solution where the pH is varied. Another example of application is the regulation of chemical or mechanical properties of a solution which vary according to the pH. One such property for example is the osmolarity of the solution.

The pH of an initial solution can conventionally be modified by mixing of an additional acid or basic solution with the initial solution. The pH of the solution finally obtained after mixing stabilizes at a value which depends on the pH of the initial solution, on the pH of the additional solution, and on the volumes of the initial and additional solutions.

However, for certain applications, it would be desirable to be able to modify the pH of a solution without having to add an acid or basic solution thereto. As an example, it would be desirable to be able to modify the pH of a solution contained in the human body, called biological solution hereafter, while limiting as much as possible any intervention on the human body to perform the pH modification.

SUMMARY OF THE INVENTION

The present invention aims at a method and a device for varying the pH of a solution which do not require the addition of an acid or basic solution.

Another object of the present invention is to provide a method for varying the pH which is likely to be implemented in a human body and a device for varying the pH which is likely to be implanted in a human body.

To achieve these objects, an aspect of the present invention provides a device for varying the pH of a solvent in which a substance is dissolved, comprising an enclosure in contact with the solvent via an enclosure wall permeable to the solvent and to the substance, the enclosure containing enzymes capable of transforming the substance to release hydrogen or hydroxyl ions, the enclosure wall being non-permeable to enzymes.

According to an embodiment, the substance is D-glucose and the enzymes are glucose oxidase enzymes capable of causing the releasing of hydrogen ions by oxidation of the D-glucose.

According to an embodiment, the substance is L-glucose and the enzymes are L-fucose dehydrogenase enzymes capable of causing the releasing of hydrogen ions by oxidation of the L-glucose.

According to an embodiment, the substance is urea and the enzymes are urease enzymes capable of causing the releasing of hydroxyl ions by ureal degradation.

Another aspect of the present invention provides an actuator comprising a device for varying the pH such as described hereabove; a first chamber connected to the device for varying the pH or corresponding to the enclosure of the device for varying the pH, and at least partially containing solvent, the device for varying the pH being capable of bringing the pH in the first chamber within a given pH range; and a second deformable chamber connected to the first chamber, the first chamber containing means capable of transferring solvent between the first chamber and the second chamber when the pH in the first chamber is within the given pH range.

According to an embodiment, the first chamber contains a solute and is separated from the second chamber by a chamber wall non-permeable to the solute and permeable to the solvent, the transformation of a precipitate of said solute into said solute or the solute precipitation being promoted when the pH in the first chamber is within the given pH range to vary the osmotic pressure in the first chamber and the second deformable chamber is capable of changing volume under the action of the solvent displacing between the first chamber and the second chamber by osmosis.

According to an embodiment, the first chamber contains a solute and is separated from the second chamber by a chamber wall non-permeable to the solute and permeable to the solvent, the transformation of a precipitate of said solute into said solute being promoted when the pH in the first chamber is within the given pH range to vary the osmotic pressure in the first chamber and the first chamber is intended to be arranged in contact with the solvent, the second chamber being capable of increasing its volume under the action of the solvent penetrating into the first chamber by osmosis.

According to an embodiment, the first chamber comprises a material capable of changing volume when the pH in the first chamber is within the given range, the material surrounding a deformable envelope containing solvent and connected to the second chamber.

An aspect of the present invention provides a motor comprising an actuator such as described previously, in which the first chamber is at least partly deformable and is connected to the second chamber at the level of the chamber wall, the transformation of the precipitate of said solute into said solute being promoted for a pH within a given acid pH range, and the precipitation of said solute being promoted for a pH within a given basic pH range, the device for varying the pH being capable of bringing the pH in the first chamber within the given acid pH range, the motor further comprising an additional device for varying the pH connected to the first chamber and capable of bringing the pH in the first chamber within the given basic pH range.

An aspect of the present invention provides a motor comprising an actuator such as described previously, in which the second chamber comprises return means which oppose the volume increase of the second chamber and controllable means for lowering the osmotic pressure in the second chamber.

An aspect of the present invention provides a motor comprising an actuator such as described previously, in which the material is capable of decreasing its volume for a pH ranging within a given acid pH range, and of increasing its volume for a pH within a given basic pH range, the device for varying the pH being capable of bringing the pH in the first chamber within the given acid pH range, the motor further comprising an additional device for varying the pH connected to the first chamber and capable of bringing the pH in the first chamber within the given basic pH range.

According to an embodiment, the second chamber is intended to surround a hollow organ of a mammal, especially the urethra, the stomach, the anus, or the heart, a volume increase of the second chamber causing a constriction of said organ.

An aspect of the present invention provides a system for purifying a substance comprising a device for varying the pH such as described hereabove, intended to be implanted in a human body in contact with a biological solvent containing said substance.

An aspect of the present invention provides a purifying system comprising a device for varying the pH such as described hereabove; a first controllable valve arranged between the enclosure wall and the solvent; a second controllable valve capable of having the enclosure of the device for varying the pH communicate with a drain; and means capable of cyclically decreasing the volume of the enclosure of the device for varying the pH when the second valve is open and the first valve is closed, whereby the content of the enclosure of the device for varying the pH is discharged through the drain, and increasing the volume of the enclosure of the device for varying the pH when the first valve is open and the second valve is closed, whereby the solvent is sucked into the enclosure of the device for varying the pH through the enclosure wall.

An aspect of the present invention provides a cell comprising an enclosure containing first and second electrodes, a reduction or oxidation reaction being likely to occur at the level of the first and of the second electrode according to the pH; a device for varying the pH capable of bringing the pH at the level of the first electrode within a given pH range promoting one of the reduction or oxidation reactions; and means capable of bringing the pH at the level of the second electrode within a second given pH range different from the first range, promoting the other one of the reduction or oxidation reactions.

According to an embodiment, the cell is intended to be arranged in contact with a solvent, said means corresponding to a valve likely to have the content of the enclosure communicate with the solvent at the level of the second electrode.

According to an embodiment, the means are an additional device for varying the pH such as described hereabove.

BRIEF DESCRIPTION OF THE DRAWINGS

The foregoing objects, features, and advantages of the present invention will be discussed in detail in the following non-limiting description of specific embodiments in connection with the accompanying drawings, among which:

FIGS. 8A to 8D show four operating steps of a third embodiment of an osmotic motor implementing the first embodiment of the device for varying the pH according to the invention;

DETAILED DESCRIPTION

Figure 1:
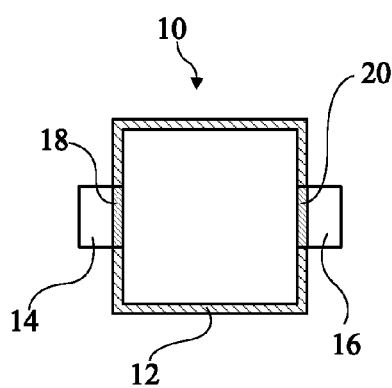
FIG. 1 shows a first embodiment of a device for varying the pH according to the invention.

The same elements have been designated with the same reference numerals in the different drawings. For clarity, only those elements which are useful to the understanding of the invention have been shown in the drawings and will be described hereafter.

The present invention provides promoting a first series or a second series of chemical reactions in a solution where the pH is desired to be modified, the first series of chemical reactions decreasing the solution pH while the second series of chemical reactions increases the solution pH.

Any reaction leading to the forming of $H^+$ ions, and thus to a pH decrease, may be appropriate for the first series of reactions. Such is in particular the case for the oxidation of D-glucose, or D stereoisomer of glucose, by the glucose oxidase enzyme, which results in the forming of gluconic acid (likely to release an $H^+$ ion) and hydrogen peroxide. Hydrogen peroxide is further degradable by the catalase enzyme or the peroxidase enzyme to provide additional $H^+$ ions. The implemented reactions are the following:

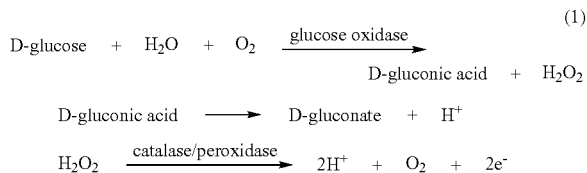

The first series of reactions may correspond to the oxidation of L-glucose, or L stereoisomer of glucose, by the L-fucose dehydrogenase enzyme. The implemented reactions are the following:

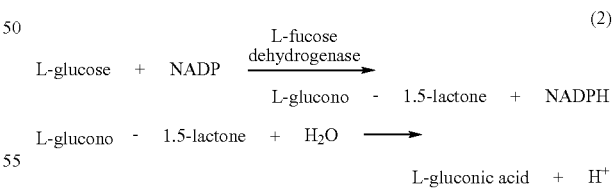

where compound NADP is nicotinamide adenine dinucleotide phosphate and where NADPH is the same compound once reduced.

The second series of reactions implemented by the present invention to basify a solution may correspond to the degradation of urea by the urease enzyme, which results in the forming of ammonium ions $NH_4^+$ and of hydroxyl ions $OH^-$, that is, in a pH increase. The implemented reactions are the following:

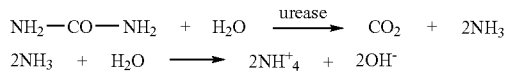

$$NH_2-CO-NH_2 + H_2O \xrightarrow{urease} CO_2 + 2NH_3$$
$$2NH_3 + H_2O \longrightarrow 2NH_4^+ + 2OH^-$$

(3)

Reactions (1) and (3) have the advantage of being directly implementable with a biological solution which naturally contains D-glucose, which is the glucose taking part in glycemia, and urea. Reactions (2) can easily be implemented with a biological solution which naturally contains the NADP compound. L-glucose then only needs to be added to the biological solution.

FIG. 1 shows a first embodiment of a device 10 for varying the pH according to the present invention. Device 10 is arranged in a solution having a pH which is desired to be modified, for example, a biological solution. Device 10 comprises a tight enclosure 12 and a valve 14 which, when open, puts the content of enclosure 12 in communication with the external solution. Device 10 may be connected to a system, not shown, having an operation which requires a solution having a pH within a determined range. For this purpose, device 10 comprises a valve 16 which, when open, puts the content of enclosure 12 in communication with the system to be supplied. Device 10 comprises a membrane 18 arranged between valve 14 and enclosure 12 and a membrane 20 arranged between valve 16 and enclosure 12. Membranes 18 and 20 have given cut-off thresholds, generally expressed in Daltons, that is, they let through particles having a molecular mass substantially smaller than the cut-off threshold.

When the solution contained in enclosure 12 is desired to be acidified, the glucose oxidation, for example, according to reactions (1), can be promoted in enclosure 12. For this purpose, device 10 is placed in a solution containing D-glucose, for example, a biological solution, and glucose oxidase enzymes and the catalase or peroxidase enzymes are placed in enclosure 12. Membranes 18 and 20 have cut-off thresholds such that they enable to retain the glucose oxidase enzymes and catalase or peroxidase enzymes in enclosure 12. Further, membrane 18 has a sufficiently high cut-off threshold to let glucose through. As an example, membranes 18 and 20 have a cut-off threshold on the order of a few hundreds of Daltons.

The operation of the first example of device 10 according to the present invention will now be described for a pH decrease operation. Initially, valve 16 is closed and valve 14 is open, enabling D-glucose to diffuse into enclosure 12. Valve 14 is then closed. The D-glucose contained in enclosure 12 is then oxidized to provide $H^+$ ions and gluconic acid according to the previously-described reactions (1). The pH of the solution contained in enclosure 12 thus decreases. The obtained acid solution can then be used by the system connected to enclosure 12 by opening valve 16. The applicant has shown that for an aqueous solution having an initial D-glucose concentration of 5.5 mmol/l, which corresponds to the average glucose concentration in the human body, a glucose oxidase enzyme concentration of 1 mg·ml$^{-1}$, that is, 47 units and an initial pH of 7, a pH equal to 5 is obtained within one hour and a pH of 3.5 is obtained after three hours in enclosure 12.

The gluconic acid resulting from the glucose oxidation tends to form salts, or gluconate, with the dissolved substances. If it is not desirable for the gluconate to penetrate in the system connected to device 10, membrane 20 is selected with a sufficiently low cut-off threshold to retain the gluconate in enclosure 12 when valve 16 is open. The cut-off threshold of membrane 20 then is on the order of 100 Daltons. At the next opening of valve 14, the gluconate diffuses outside of enclosure 12. In the case of a medical application for which device 10 is placed in the human body, it is desirable for the catalase or peroxidase enzymes to be placed at the level of membrane 18 to avoid the releasing of free radicals resulting from the D-glucose oxidation into the human body. Further, the releasing of gluconate into the human body is not dangerous since it is naturally discharged by the kidneys.

For a solution acidification operation, L-fucose dehydrogenase enzymes, retained by membranes 18 and 20, may be arranged in enclosure 12. Device 10 is then placed in a solution containing L-glucose, the device operation being identical to what has been previously described. A human biological solution does not naturally comprise L-glucose. In the case where device 10 is placed in the human body, a step of addition of L-glucose to the biological solution, for example by intravenous injection, may be provided.

Device 10 according to the first embodiment of the invention may also be used to obtain a pH increase. Device 10 is then arranged in a solution containing urea, for example a biological solution, and the degradation of urea into ammonia and into carbonic acid according to reactions (3) is promoted in enclosure 12. Since ammonia reacts with water to provide ammonium ions, a pH increase is thus obtained. For this purpose, urease enzymes are placed in enclosure 12. In this case, membranes 18 and 16 have a sufficiently low cut-off threshold to retain the urease enzymes in enclosure 12. Further, membrane 18 has a sufficiently high cut-off threshold to let through urea, which has a 60 g/mol molecular mass. As an example, membrane 18 has a cut-off threshold of a few hundreds of Daltons. The operating cycle of device 10 is then identical to what has been previously described. The applicant has shown that for a solution having a 3 mmol/l urea concentration, which corresponds to the average urea concentration in the human body, and an initial pH of 7, a pH equal to 8.2 is obtained within two hours and a pH of 9.2 is obtained after one night in enclosure 12. In the case of a medical application for which device 10 according to the invention is placed in the human body, the carbon dioxide resulting from reactions (3) is naturally exhaled. Further, the ammonium ions resulting from reactions (3) are metabolized by the liver.

Figure 2:
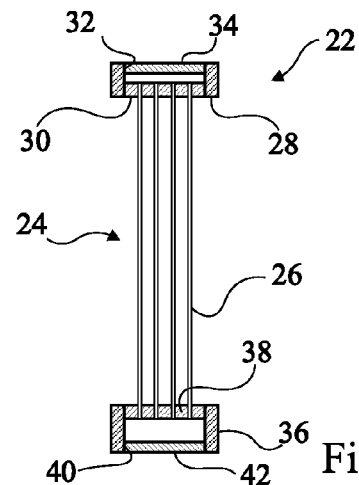
FIG. 2 shows a second embodiment of the device for varying the pH according to the invention.

FIG. 2 shows a second embodiment of a device 22 for varying the pH according to the invention. Device 22 comprises an enclosure 24 formed of a bundle of hollow fibers with a semi-permeable wall 26, for example of the type used for dialysis operations. Each fiber for example has a diameter on the order of 200 μm. Fiber bundle 26 is maintained at a first end by a first connection ring 28, for example, via a gluing area 30. Ring 28 comprises an opening 32 closed by a plug 34. The second end of fiber bundle 26 is maintained by a second connection ring 36, for example, via a gluing area 38. Second ring 36 comprises an opening 40 closed by a plug 42.

Device 22 is intended to be immersed in the solution where the pH is desired to be modified. The diameter and the length of the fibers are adapted according to the desired exchange surface area between fiber bundle 26 and the solution in which device 22 has been immersed. If the pH is desired to be decreased, glucose oxidase and catalase or peroxidase enzymes are placed in fibers 26 via openings 32, 40, which are then closed by plugs 34, 42. The wall of fibers 26 then has a cut-off threshold such that it does not let through glucose oxidase enzymes and catalase or peroxidase enzymes, which are retained in fiber bundle 26, while it lets through D-glucose and gluconate. If the pH is desired to be increased, urease enzymes are arranged in fibers 26 via openings 32, 40 which are then closed by plugs 34, 42. The wall of fibers 26 then has a cut-off threshold such that it does not let through urease enzymes, which are retained in fiber bundle 26, while it lets through urea.

When device 22 is implanted in the human body to acidify a biological solution, the catalase or peroxidase enzymes are preferably fixed on the internal wall of fibers 26 while the glucose oxidase enzyme can be left free in fiber bundle 26. Such an arrangement enables to avoid for the free radicals created by the degradation of glucose by the D-glucose oxidase enzymes to cross the wall of fibers 26 and spread in the biological solution.

When device 10, or device 22, is used to acidify a solution implementing the oxidation of D-glucose, it simultaneously enables the suppression of part of the D-glucose contained in the solution. Indeed, the reactions implemented in enclosure 12 or in fiber bundle 26 (reactions (1)) result in the transformation of glucose into gluconic acid, which provides gluconate. Such a device 10 (or 22) may be implanted in the human body to suppress an excess of D-glucose, generally associated with a type-I or type-II diabetes or with an overweight. Several locations of implantation of device 10 (or 22) can then be envisaged. As an example, device 10 (or 22) may be placed at the level of the peritoneum or of a fatty peri-cellular space. An implantation close to the peritonea has the advantage of a rich vascularization and of a high D-glucose concentration. An implantation in a fatty space decreases risks of inflammatory responses. Device 10 (or 22) may also be implanted at the level of a muscle, by a puncture performed by means of a medical trocart.

As soon as it has been implanted in the human body, device 22 according to the present invention daily transforms a quantity of D-glucose into gluconate which is naturally removed by the kidney. Device 10 itself enables, by the controlling of valves 14, 16, to control the amount of D-glucose transformed into gluconate. Via valves 14, 16 (respectively openings 32, 40), it is possible to have access to the content of enclosure 12 (respectively of fibers 26) to renew the enzyme population contained in enclosure 12 (respectively in fibers 26) if necessary. The implantable chambers conventionally used for chemotherapies allow a very easy percutaneous puncture, due to which this renewal can be performed. This enables to overcome a lower enzymatic activity. Further, the access to the content of enclosure 12 (respectively of fibers 26) also enables to regulate the enzyme population to control the consumed glucose amount.

Figure 3A:
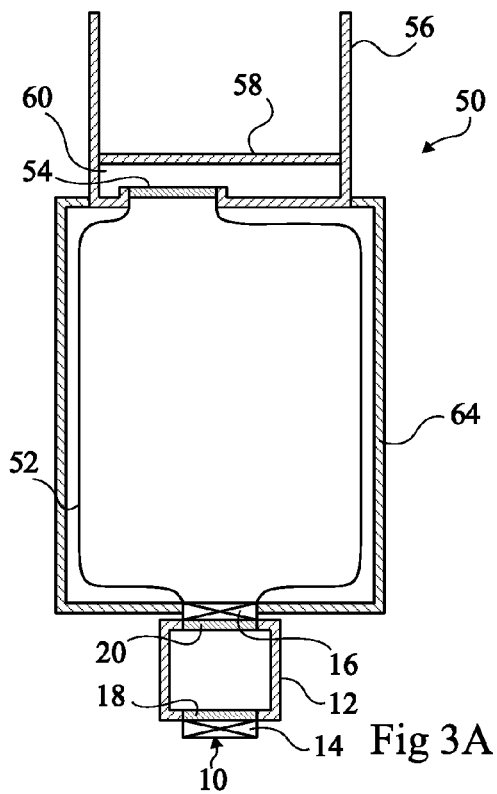
FIGS. 3A and 3B show two operating steps of an embodiment of an osmotic actuator implementing the device for varying the pH according to the first embodiment.
Figure 3B:
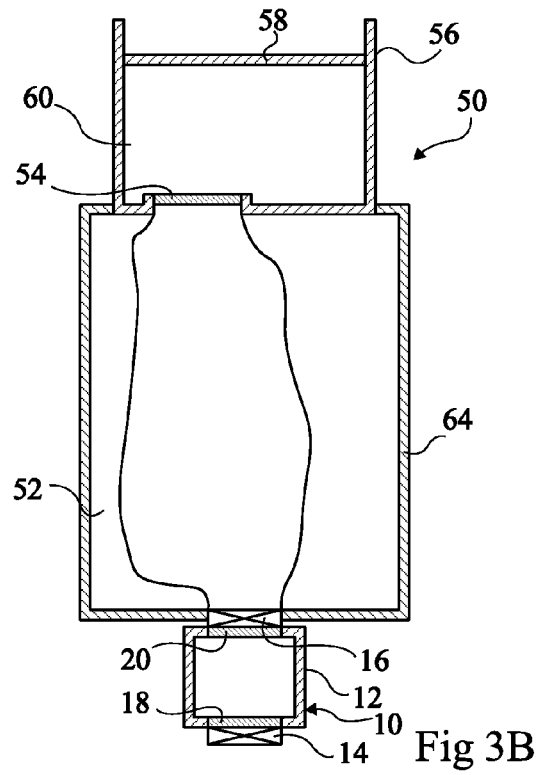

FIGS. 3A and 3B show an embodiment of an osmotic actuator 50 implementing the first embodiment of device 10 for varying the pH according to the invention. Osmotic actuator 50 comprises a tight deformable envelope 52 filled with a solvent and connected to device 10 at the level of valve 16. Envelope 52 is further connected via a membrane 54 to a cylindrical body 56 in which a piston 58 can slide. Piston 58 and cylindrical body 56 define an expansion chamber 60. Envelope 52 may be arranged in a rigid housing 64 which is perforated so that deformations of envelope 52 are not hindered by a vacuum which might install between envelope 52 and housing 64, if the latter was tight.

Expansion chamber 60 contains a substance A, dissolved in the solvent and osmotically active and at a concentration enabling an osmotic balance with the inside of envelope 52. Membrane 54 has a sufficiently low cut-off threshold to block substance A. As an example, substance A is dextrane. Device 10 for varying the pH is of the type enabling to basify the solution that it contains, as described previously. Envelope 52 contains an osmotically-active substance Z. Membrane 54 has a sufficiently low cut-off threshold to block substance Z. As an example, substance Z is chitosan, which is soluble in water at an acid pH, and insoluble at a basic pH. The pH variation of the solution thus causes a variation of the number of dissolved molecules and accordingly of the osmolarity of the solution.

The operation of osmotic actuator 50 according to the present invention will now be described. It is a single-stroke actuator.

FIG. 3A shows osmotic actuator 50 in the state which precedes the actuator operation. Valve 16 is then closed. Envelope 52 has a maximum volume while expansion chamber 60 has a minimum volume. The concentrations of substances A and Z are initially selected so that the osmotic pressures in expansion chamber 60 and in envelope 52 are balanced, with piston 58 remaining idle. Before the operation of actuator 50, device 10 for varying the pH is controlled, as described previously, so that enclosure 12 contains a basic solution.

When osmotic actuator 50 is desired to be operated, valve 16 is opened. The OH$^-$ ions contained in enclosure 12 expand into envelope 52, thus increasing the pH of the solvent contained in envelope 52. When the pH in envelope 52 has increased up to the desired value, valve 16 is closed. The precipitation of substance Z is then promoted. The osmotic pressure in envelope 52 decreases with respect to the osmotic pressure in expansion chamber 60, which does not vary. A solvent transfer thus occurs, with solvent passing from envelope 52 to expansion chamber 60 through membrane 54, thus causing a displacement of piston 58. Piston 58 is in its upward phase.

FIG. 3B shows osmotic actuator 50 at the end of the upward phase of piston 58. Expansion chamber 60 then has a maximum volume. Piston 58 may be connected to an external element to which mechanical power is desired to be transmitted.

In the previously-described example of actuator 50, device 10 is of a type enabling to basify the solution that it contains. However, actuator 50 may also be implemented with a device 10 capable of acidifying the solution that it contains. In this case, initially, expansion chamber 60 may have a maximum volume and envelope 52 may have a minimum volume, as shown in FIG. 3B. When valve 16 is opened, the pH of the solvent in envelope 52 and expansion chamber 60 decreases, promoting the solubilization of substance Z present in envelope 52. The osmotic pressure in envelope 52 increases with respect to the osmotic pressure in expansion chamber 60, which does not vary. A solvent transfer thus occurs, with solvent passing from expansion chamber 60 into envelope 52 through membrane 54, causing, by suction, a displacement of piston 58. Piston 58 is then in its downward phase until expansion chamber 60 has a minimum volume, as shown in FIG. 3A.

An example of application of actuator 50 is the inflating of a joint associated with an endoprosthesis corresponding to a small spring, or stent, slid into a cavity of the human body (arteries, for example) to maintain it open. Indeed, joints may be provided at the ends of the stent and may be inflated by means of actuator 50, after the stent has been installed, to maintain the tightness at the stent ends in the case of a subsequent unwanted deformation of the cavity containing the stent.

FIGS. 4A to 4D show a first embodiment of an osmotic motor 70 according to the invention. Osmotic motor 70 comprises certain components of actuator 50 shown in FIGS. 3A and 3B and the corresponding reference numerals are kept. Return means 72, for example, a spring, exerts on piston 58 a pulling force tending to bring it back to an idle position. Motor 70 comprises two devices for varying the pH, noted 10 and 10'. In the following description, dashed reference numerals are used to designate the elements of device 10' for varying the pH, to differentiate them from the elements of device 10 for varying the pH. Envelope 52 is connected to device 10' at the level of valve 16'. Device 10 is of the type enabling to decrease the pH of the solution that it contains and device 10' is of the type enabling to increase the pH of the solution that it contains.

Envelope 52 contains, as described previously, substance Z likely to solubilize in the presence of H$^+$ ions, the inverse reaction according to which substance Z precipitates being likely to occur in the presence of OH$^-$ ions. As described previously for osmotic actuator 50, expansion chamber 60 contains an osmotically-active substance A, dissolved in the solvent. Membrane 54 has a sufficiently low cut-off threshold to prevent the passing of substance A and Z.

An operating cycle of motor 70 according to the invention will now be described.

Figure 4A:
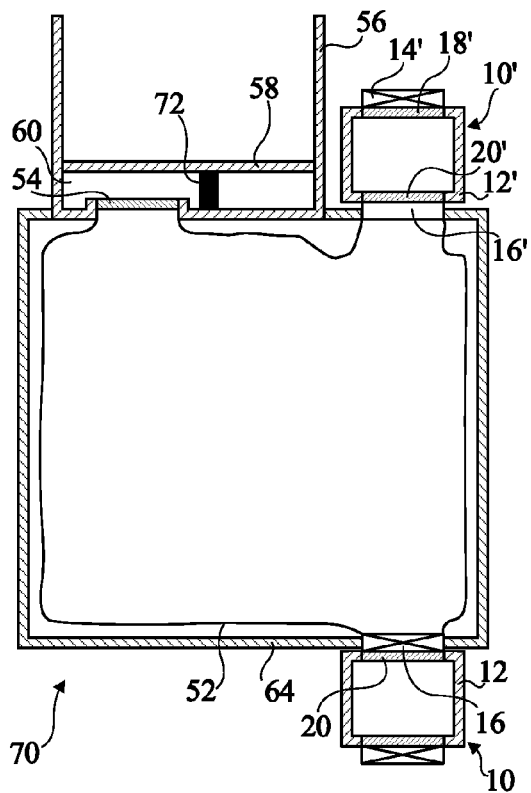
FIGS. 4A to 4D show four operating steps of a first embodiment of an osmotic motor implementing the first embodiment of the device for varying the pH according to the present invention.

FIG. 4A shows motor 70 at the beginning of a cycle. Envelope 52 has a maximum volume and chamber 60 has a minimum volume. The concentrations of substances A and Z are initially selected so that the osmotic pressures in expansion chamber 60 and in envelope 52 are balanced, with piston 58 remaining idle. During the opening cycle of valves 16 and 16' which will now be described, devices 10, 10' are controlled so that enclosures 12, 12' contain solutions having the desired pH.

Valve 16 is closed and valve 16' is opened. The OH$^-$ ions disseminate into envelope 52, thus increasing the pH of the solvent contained in envelope 52 and in expansion chamber 60. When the pH in envelope 52 has increased up to the desired value, valve 16' is closed. The precipitation of substance Z is then promoted. The osmotic pressure in envelope 52 decreases with respect to the osmotic pressure in expansion chamber 60, which does not vary. A solvent transfer thus occurs, with solvent passing from envelope 52 into expansion chamber 60 through membrane 54, thus causing a displacement of piston 58. Piston 58 is in its upward phase.

Figure 4B:
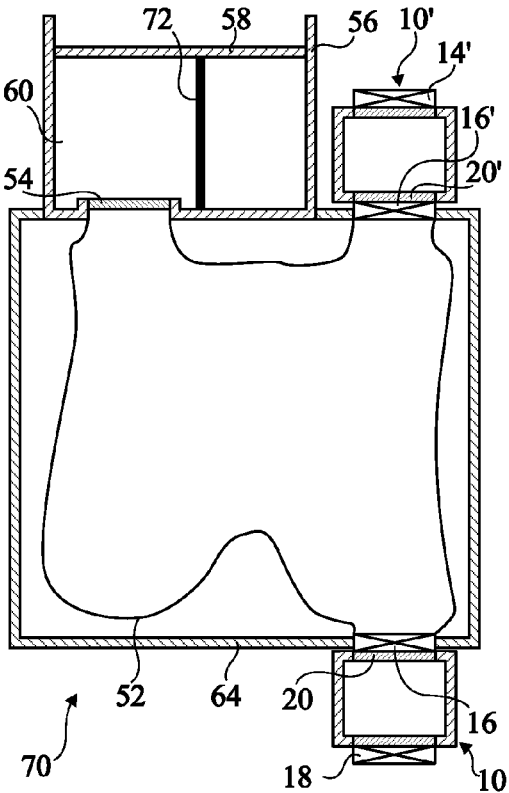

FIG. 4B shows motor 70 at the end of the upward phase of piston 58. Chamber 60 thus has a maximum volume.

Figure 4C:
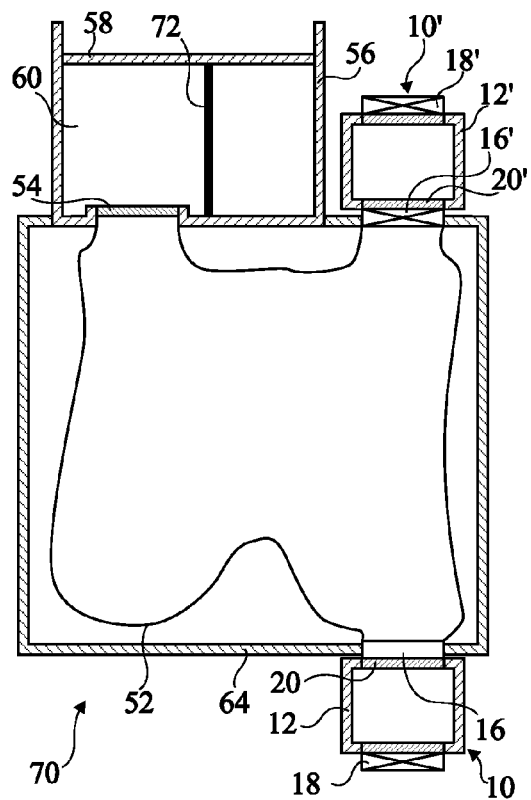

In FIG. 4C, valve 16 has been opened to put the content of envelope 52 in communication with the content of enclosure 12. H$^+$ ions disseminate into envelope 52, thus causing a decrease in the pH of the solvent contained in envelope 52 as well as in expansion chamber 60. When the pH is sufficiently acid, valve 16 is closed. The solubilization of substance Z is then promoted, thus causing an increase in the number of dissolved osmotically-active particles in envelope 52. With the osmotic pressure increase in envelope 52, a new solvent transfer occurs, with solvent passing from expansion chamber 60 into envelope 52 via membrane 54. The action of spring 72 promotes the discharge of the solvent from expansion chamber 60. However, spring 72 might be absent, and piston 58 would then only be displaced by suction. Piston 58 is said to be in its downward phase.

Figure 4D:
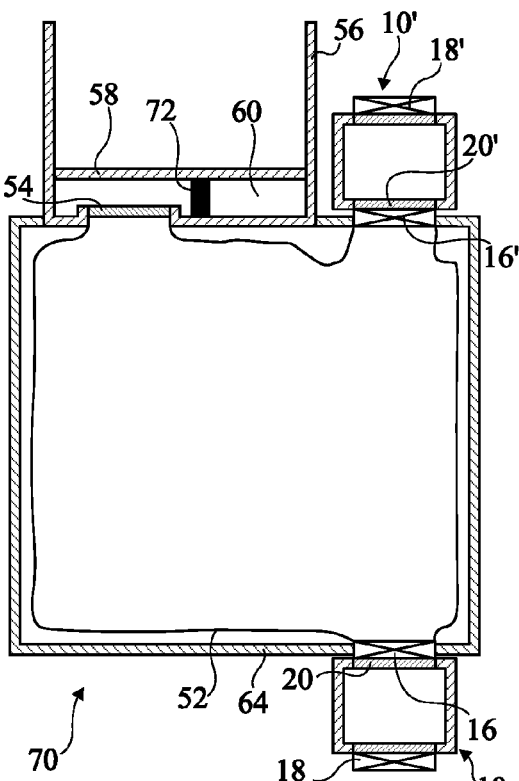

FIG. 4D shows motor 70 at the end of the downward phase of piston 58, which closes the cycle. The concentrations of substances Z and A, respectively in envelope 52 and in expansion chamber 60, are then substantially identical to the concentrations at the beginning of a cycle.

Figure 5A:
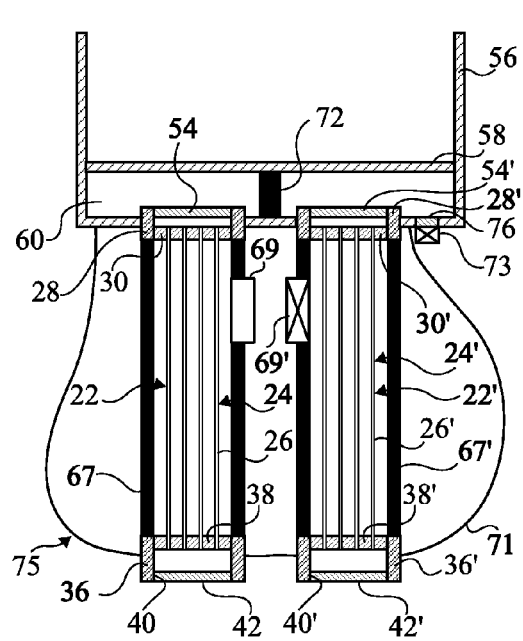
FIGS. 5A and 5B show two operating steps of a second embodiment of an osmotic motor implementing the second embodiment of the device for varying the pH according to the present invention.
Figure 5B:
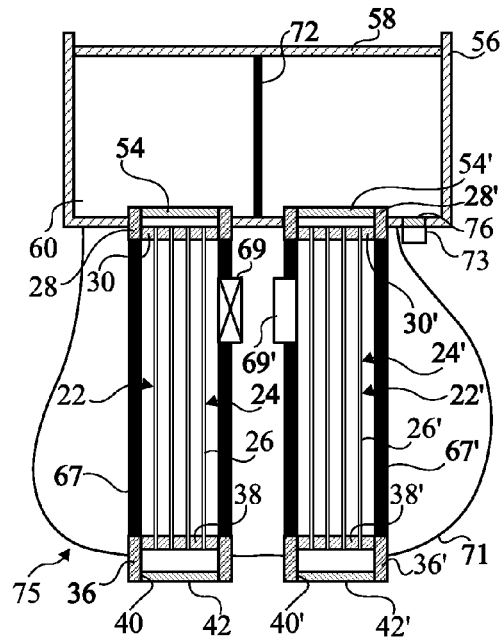

FIGS. 5A and 5B show a second embodiment of an osmotic motor 75 implementing the second embodiment of device 22 for varying the pH according to the invention and certain elements of osmotic motor 70. Motor 75 comprises two devices for varying the pH, noted 22 and 22'. In the following description, dashed reference numerals are used to designate the elements of device 22' for varying the pH, to differentiate them from the elements of device 22 for varying the pH. Each device 22, 22' for varying the pH communicates with expansion chamber 60 at the level of membrane 54, 54' which replaces plug 34. Further, device 22 for varying the pH is contained in a tight enclosure 67 which connects connection rings 28 and 36, and device 22' for varying the pH is contained in a tight enclosure 67' which connects connection rings 28' and 36'. A valve 69, 69' is provided at the level of enclosure 67, 67'. Enclosures 67, 67' are contained in an semi-permeable envelope 71 which is connected to cylindrical body 56 and to connection rings 36, 36' of devices 22, 22' for varying the pH. Cylindrical body 56 comprises a discharge valve 73 which connects the expansion chamber to the outside of motor 75 via a membrane 76.

As an example, device 22' is of the type enabling to decrease the pH of the solution in which it is arranged according to the previously-described reactions (1), glucose oxidase enzymes being arranged in fibers 26'. Device 22 is of the type enabling to increase the pH of the solution in which it is arranged according to the previously-described reactions (3), urease enzymes being arranged in fibers 26.

Compound Z, such as previously described, likely to solubilize in an acid medium, is further arranged in envelope 71. The cut-off threshold of fibers 26 enables to prevent the passing of substances A and Z and of urease enzymes. The cut-off threshold of membrane 54 enables to prevent the passing of urease enzymes but lets through substance A. Further, the cut-off threshold of fibers 26' enables to prevent the passing of substances A and Z and of glucose oxidase enzymes. The cut-off threshold of membrane 54' enables to prevent the passing of glucose oxidase enzymes but lets through substance A. The cut-off threshold of envelope 71 enables to prevent the passing of substance Z. The cut-off threshold of membrane 76 enables to prevent the passing of substance A.

In normal operation, motor 75 is placed in a solution containing glucose and urea. The cut-off threshold of fibers 26' is sufficiently high to enable the passing of glucose and the cut-off threshold of fibers 26 is sufficiently high to enable the passing of urea. Further, the cut-off threshold of envelope 71 is sufficiently high to enable the passing of the solvent, of glucose, and of urea. The concentrations of substances A and Z are initially selected so that the osmotic pressures in expansion chamber 60 and in envelope 71 are balanced, with piston 58 remaining idle.

An operating cycle of motor 75 will now be described.

FIG. 5A shows motor 75 at the beginning of a cycle. Piston 58 is in idle position, the volume of expansion chamber 60 being minimum. Discharge valve 73 is closed, valve 69' is closed, and valve 69 is open. As soon as motor 75 is placed in the solution containing urea, the urea crosses envelope 71 and expands into fibers 26. The ureal degradation provides OH$^-$ ions which disseminate into envelope 71. The pH increase in envelope 71 promotes the precipitation of substance Z, which tends to lower the osmotic pressure in envelope 71. The osmotic pressure variation creates a liquid flow from the inside of envelope 71 to expansion chamber 60 via fibers 26, thus displacing piston 58. The displacement 58 stretches spring 72, thus enabling to store mechanical power.

In FIG. 5B, expansion chamber 60 is shown in maximum expansion. Valve 69 is then closed and valve 69' is open. Further, discharge valve 73 is open. The pressure within expansion chamber 60 equalizes with the ambient pressure. Spring 72 brings piston 58 back to its idle position, thus chasing, through discharge valve 73, the solvent from expansion chamber 60 in to the environment. The mechanical power stored in spring 72 is thus recovered. Further, valve 69' being open, glucose penetrates into fibers 26'. The degradation of glucose provides H+ ions which disseminate into envelope 71. The pH decrease in envelope 71 promotes the solubilization of substance Z, which enables to return to the concentrations of substance Z of the beginning of the cycle. Valve 73 is finally closed, thus ending the motor stroke.

In the present embodiment, expansion chamber 60 is defined by a cylindrical body 56 in which a piston 58 slides. Depending on the desired use of motor 75 according to the present invention, expansion chamber 60 may be different.

Figure 6A:
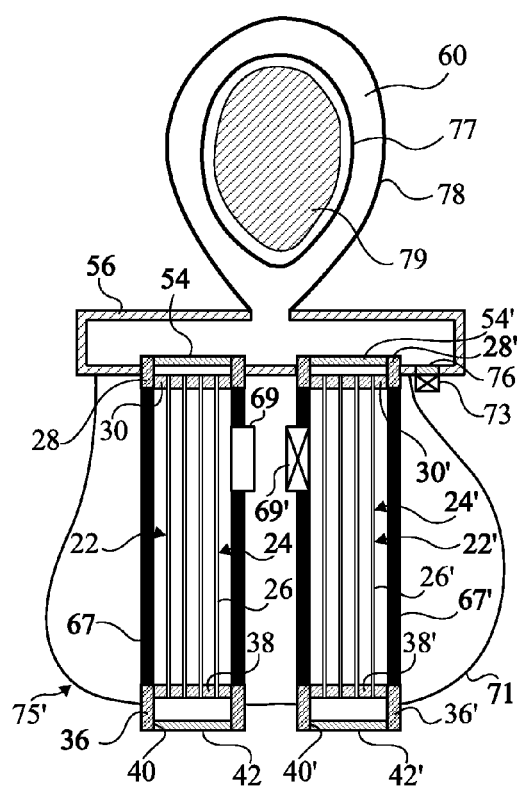
FIGS. 6A and 6B show two operating steps of a variation of the second embodiment of the osmotic motor.
Figure 6B:
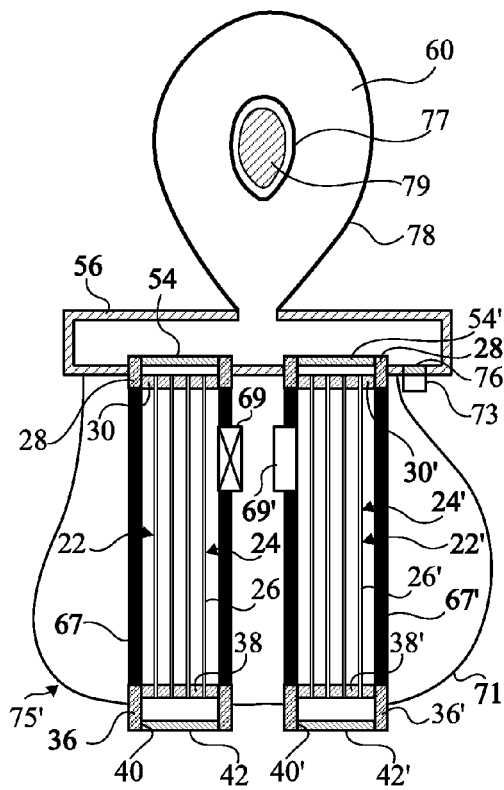

FIGS. 6A and 6B show an osmotic motor 75' implementing an alternative structure of expansion chamber 60 of motor 75 of the preceding embodiment. According to this variation, expansion chamber 60 corresponds to the space defined between an inner envelope 77 and an outer envelope 78, just like an air tube. Inner envelope 77 is deformable and extensible and surrounds a deformable body 79. Outer envelope 78 is flexible and inextensible. It closes back onto inner envelope 77 and is connected to cylindrical body 56. As an example, in a medical application of osmotic motor 75' according to the present invention, deformable body 79 may be a hollow organ of the human body such as the stomach, the urethra, the anus, or the heart and envelopes 77, 78 may define bead-shaped expansion chambers 60 surrounding the hollow organ. The osmotic motor then behaves as a mover of an artificial sphincter (when the hollow organ is the urethra or the anus) or of an adjustable gastric band (when the hollow organ is the stomach).

A cycle of motor 75' according to the present variation will now be described.

FIG. 6A shows motor 75' at the beginning of a cycle. The volume of expansion chamber 60 is minimum, deformable body 79 being in maximum expansion, which may correspond to a urethra or to an anal canal or to a stomach at maximum "opening" or to a heart in diastole. Discharge valve 73 is closed, valve 69' is closed and valve 69 is open. The urease enzymes promote the ureal degradation and the pH increase in envelope 71, which promotes the precipitation of substance Z. This causes, by osmosis, the introduction of solvent into expansion chamber 60. Inner envelope 77 deforms and compresses deformable body 79.

In FIG. 6B, deformable body 79 is at maximum compression, which may correspond to a "closed" urethra, to a "closed" anal canal, to a stomach at minimum "opening", or to a heart in systole. Valve 69' is then open and valve 69 is closed. At the opening of discharge valve 73, the solvent leaves expansion chamber 60, thus enabling the expansion of deformable body 79, which ends the cycle.

According to another variation of the invention, the expansion chamber is formed of an additional resilient envelope enclosing fibers which are for example arranged in a spiral and which are connected at an end to cylindrical body 56. When solvent penetrates into the fibers, said fibers tend to straighten up and to deform the resilient envelope. At the opening of valve 73, the pressure within the fibers decreases and the additional envelope tends to recover its initial shape.

According to another variation of the invention, the device for varying the pH may be connected to the deformable chamber by a flexible duct. This enables to advantageously arrange the device for varying the pH in an environment suitable for the supply of a solvent in which the used substances (glucose or urea, for example) are dissolved by the enzymes contained in the device for varying the pH, and to place the expansion chamber at a location where mechanical power is desired to be available. In the case of a medical application, the device for varying the pH may be arranged in a fatty tissue, or on the vascular network. In this last case, the fibers may be arranged to form a hollow tube, leaving at its center a cylindrical space enabling the flowing of a fluid such as blood. The connection rings may be torus-shaped and placed against the wall of a blood vessel. One of the toric connection rings communicates with the expansion chamber by the flexible duct which perforates the blood vessel.

Figure 7A:
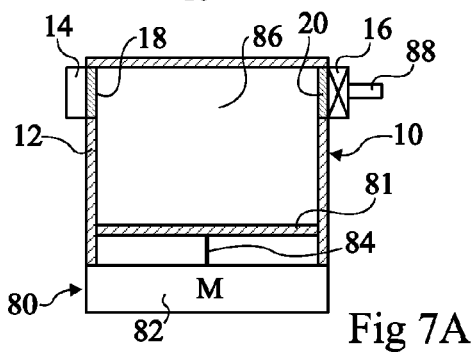
FIGS. 7A and 7B show two operating steps of a purifying device implementing the first embodiment of the device for varying the pH according to the invention.
Figure 7B:
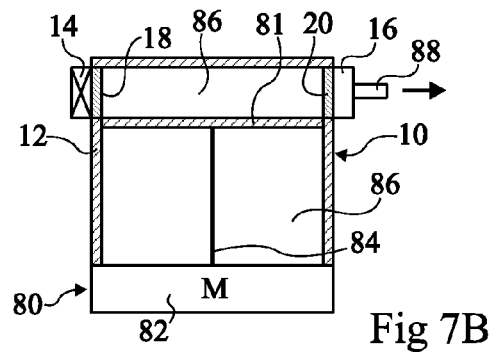

FIGS. 7A and 7B show a variation of device 10 for varying the pH according to the first embodiment of the invention. According to such a variation, a piston 81 capable of sliding in enclosure 12 is provided in enclosure 12. Piston 81 is driven by a motor (M) 82, for example, osmotic motor 70 described in relation with FIGS. 4A to 4D. Reference 84 designates an element of connection between piston 81 and motor 82, for example, return means. Piston 81 and enclosure 12 define a chamber of variable volume 86. A drain 88 is connected to valve 16.

The privileged reaction in chamber 86 is the pH increase by ureal degradation (reactions (3)). Urease enzymes are then arranged in chamber 86. Membranes 18, 20 have a cut-off threshold enabling to retain urease enzymes in chamber 86. Device 80 is adapted to an application according to which, in parallel with the pH increase, excess urea is desired to be removed from the solution in which device 80 is placed.

An operating cycle of device 80 according to the invention will now be described.

FIG. 7A shows device 80 at the beginning of a cycle. The volume of chamber 86 is maximum, valve 14 is open and valve 16 is closed. The solution contained in chamber 86 substantially corresponds to the solution in which device 80 is arranged. Valve 14 is then closed. The urea degradation reaction takes place in chamber 86, thus increasing the pH of the solution contained in chamber 86. Motor 82 is then actuated to displace piston 81, thus decreasing the volume of chamber 86. Valve 16 is open during the displacement of piston 81, thus causing the discharge of the solution contained in chamber 86 via duct 88.

FIG. 7B shows device 80 at the end of the upward phase of piston 81. Chamber 86 then has a minimum volume. Valve 16 is then closed. Motor 82 is then actuated to displace piston 81, thus causing a volume increase of chamber 86. Valve 14 is open during the displacement of piston 81, causing the suction into chamber 86 of the solution in which device 80 is placed. The cycle ends when chamber 86 has a maximum volume.

Such a device 80 may be implanted in the human body for the removal of excess urea. The ammonium ions obtained in ureal degradation are then likely to react with elements such as magnesium, calcium, and potassium present in a biological solution to form solid compounds. It may then not be desirable to reject such solid compounds outside of device 80 into the biological solution. For this purpose, drain 88 is connected to a region likely to receive the waste resulting from ureal degradation, for example, at the level of the colon.

FIGS. 8A to 8D show a third embodiment of an osmotic motor 90 according to the invention. Osmotic motor 90 comprises certain components of the first example of osmotic motor 70 shown in FIGS. 4A to 4D and the corresponding reference numerals are kept.

As compared with osmotic motor 70, envelope 52 and membrane 54 are no longer present. Housing 64 contains a polymer gel 92 capable of changing volume according to the pH. It for example is a polymer gel reversible according to the pH such as described in the works of Y. Osada (Polymer Gels and Networks, Yoshihito Osada and Alexi R. Khokhlov, New York, Marcel Dekker Inc., 2001, 400 p.), which increases volume when the pH increases. A tight envelope 94 is arranged in housing 92 and communicates with expansion chamber 60. Envelope 94 and expansion chamber 60 are filled with a solvent, for example, an aqueous solution.

An operating cycle of motor 90 will now be described.

FIG. 8A shows motor 90 at the beginning of a cycle. Gel 92 takes up a minimum volume. Envelope 94 thus has a maximum volume and chamber 60 has a minimum volume. In parallel to the opening cycle of valves 16 and 16' which will now be described, devices 10, 10' are controlled so that enclosures 12, 12' contain solutions having the desired pH.

Valve 16 is closed and valve 16' is open. $OH^-$ ions disseminate into housing 64, thus increasing the pH. Gel 92 then increases volume and compresses envelope 94. When the pH in envelope 52 has increased up to the desired value, valve 16' is closed. The volume decrease of envelope 94 causes a solvent transfer from envelope 94 into expansion chamber 60, thus causing the displacement of piston 58. Piston 58 is in its upward phase.

FIG. 8B shows motor 90 at the end of the upward phase of piston 58. Chamber 60 then has a maximum volume.

In FIG. 8C, valve 16 has been opened to put the content of housing 64 in communication with the content of enclosure 12. $H^+$ ions disseminate into housing 64, thus decreasing the pH in housing 64. When the pH is sufficiently acid, valve 16 is closed. The volume decrease of gel 92 is then promoted, thus causing the volume increase of envelope 94. A new solvent transfer occurs, with solvent passing from expansion chamber 60 into envelope 94. The action of spring 72 promotes the discharge of the solvent from expansion chamber 60. However, spring 72 may not be present, and piston 58 would then only be displaced by suction. Piston 58 is said to be in its downward phase.

FIG. 8D shows motor 90 at the end of the downward phase of piston 58, which ends the cycles.

The use of gel 92 having a volume which varies according to the pH may be implemented to form a single-stroke actuator. As an example, as compared with motor 90, only device 10' is present. The actuator operation is then identical to what has been previously described for motor 90 in relation with FIGS. 8A and 8B. According to another example, as compared with motor 90, only device 10 is present. The actuator operation is then identical to what has been previously described for motor 90 in relation with FIGS. 8C and 8D.

According to a variation of previously-described actuators and osmotic motors 70, 90, membranes 20, 20' and 54 may be replaced with a bundle of fibers or a similar system if the exchange surface area between the content of enclosure 12, 12' and the content of housing 64 or between the content of envelope 52 and the content of expansion chamber 60 is desired to be increased.

Figure 9A:
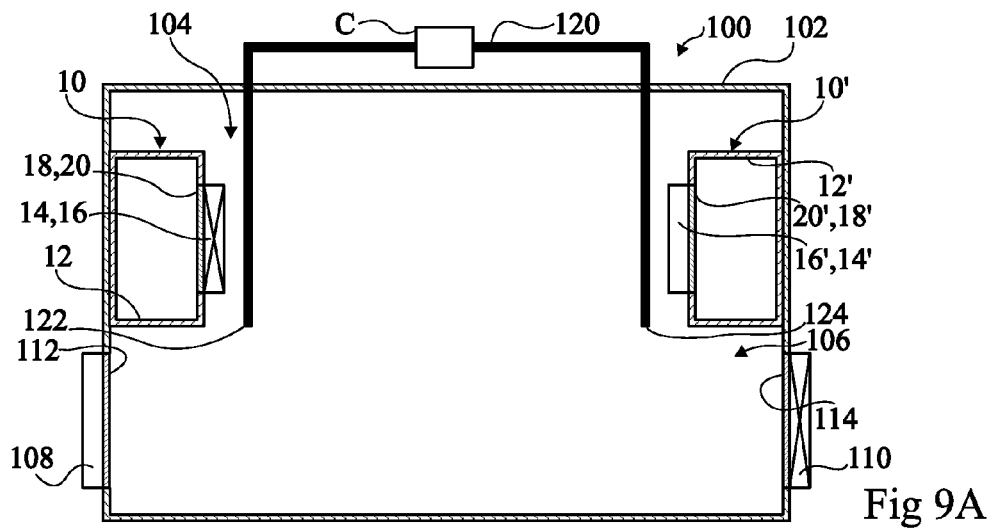
FIGS. 9A and 9B show two operating steps of a first embodiment of an electric cell implementing the first embodiment of the device for varying the pH according to the invention.
Figure 9B:
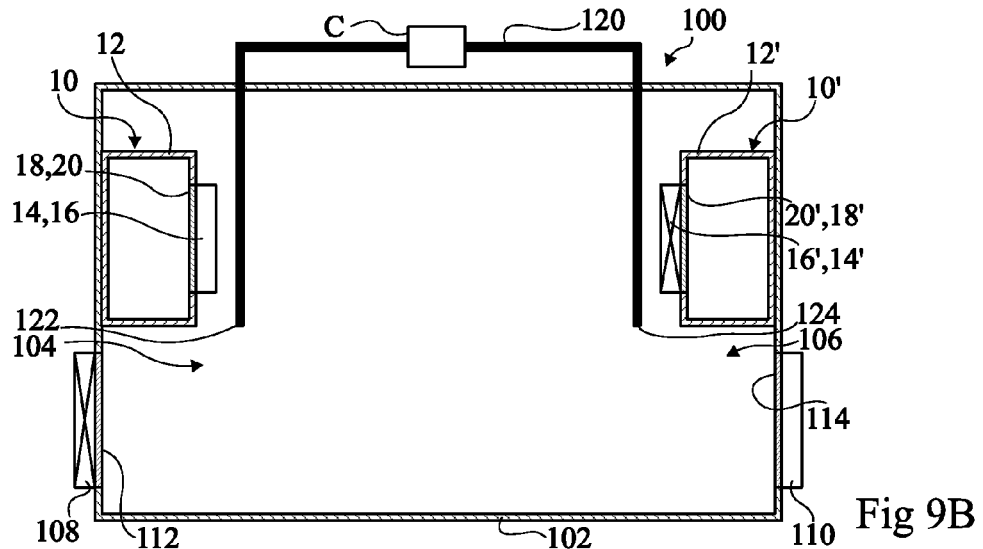

FIGS. 9A and 9B show a first embodiment of a cell 100 implementing the first example of the device for varying the pH according to the invention. Cell 100 is intended to operate in a biological solution. It comprises a tight enclosure 102 comprising two regions 104, 106 which communicate together. A valve 108, when opened, puts in communication the content of enclosure 102, on the side of region 104, with the external solution. A valve 110, when opened, puts in communication the content of enclosure 102, on the side of region 106, with the external solution. Cell 100 comprises a membrane 112 arranged between valve 108 and enclosure 102 and a membrane 114 arranged between valve 110 and enclosure 102.

Cell 100 comprises a first device 10 for varying the pH, arranged at the level of region 104, for which, with respect to what has been shown in FIG. 1, valves 14 and 16 are confounded and membranes 18, 20 are confounded. Further, cell 100 comprises a second device for varying the pH, arranged at the level of region 106. In the following description, dashed reference numerals are used to designate the elements of the device for varying the pH to differentiate them from the elements of first device 10 for varying the pH. Devices 10 and 10' are of the type enabling to decrease the pH of the solution that it contains. As an example, devices 10, 10' enable an acidification of the solution contained in associated enclosure 12, 12' according to the previously-described reactions (1).

A conductive element 120 connects region 104 of enclosure 102 and region 106 of enclosure 102 via a load C intended to be powered by cell 100. Conductive element 120 is continued by an electrode 122 that may for example be made of ferric hydroxide $Fe(OH)_3$ in region 104 of enclosure 102 and by a ferric hydroxide electrode 124 in region 106 of enclosure 102.

Cell 100 is placed in a solution containing D-glucose, for example, a biological solution, and having a substantially neutral or possibly slightly acid or basic pH. Membranes 112, 114 are capable of letting through D-glucose and gluconate. However, membranes 112, 114 do not let through positive ions. For this purpose, membranes 112, 114 may be positively charged. An example of positively-charged membranes may be obtained by techniques such as those used by ASTOM corporation. Membranes 112, 114 thus let through negative ions of small dimensions, such as hydroxyl ions $OH^-$ and bicarbonate ions $HCO_3^-$.

According to a variation, membranes 20, 20', 112, and 114 may be replaced by a fiber bundle or an analog system if the exchange surface area between the content of enclosure 12, 12' and the content of housing 102 or between the content of housing 102 and the environment is desired to be increased. Further, several valves (and the associated membranes) controlled in the same way as valve 108 may be distributed on housing 102 at the level of region 104. Similarly, several valves (and the associated membranes) controlled in the same way as valve 110 may be distributed on housing 102 at the level of region 106. Further, several valves (and the associated membranes) controlled in the same way as valve 14 may be distributed on enclosure 12 of device 10. Similarly, several valves (and the associated membranes) controlled in the same way as valve 14' may be distributed on enclosure 12' of device 10'.

FIG. 9A shows cell 100 in a first operating phase. Valve 108 is open and valve 110 is closed. Further, valve 14 is closed and valve 14' is open. D-glucose thus penetrates into enclosure 12' of device 10'. Previously-described reactions (1), which take place in enclosure 12', cause the release of $H^+$ ions which disseminate outside of device 10', into region 106 of enclosure 102, and in particular at the level of electrode 124. The cell operation is based on oxidation-reduction reactions which are more or less promoted according to the pH. More specifically, in the first operating phase, electrode 124 behaves as a cathode. The presence of $H^+$ ions at the level of cathode 124 promotes the following reduction reaction:

$$Fe(OH)_3 + 3H^+ + e^- \rightarrow Fe^{2+} + 3H_2O \qquad (4)$$

Since valve 14 is closed, device 10 releases no $H^+$ ions into region 104 of enclosure 102. Further, since valve 110 is closed and valve 108 is open, the establishment of a pH gradient between region 104 and region 106 of enclosure 102 is promoted, the pH being higher in region 104 than in region 106. Indeed, the $H^+$ ions which propagate to region 104 for example tend to react with $OH^-$ hydroxyl ions present in the biological solution and crossing membrane 112 to form water or with $HCO_3^-$ bicarbonate ions to form water and carbon dioxide.

The Fe$^{2+}$ ions which form at cathode 124, are trapped in enclosure 102 and migrate to electrode 122 which behaves as an anode. The communication with the outside through valve 108 enables the pH to remain close to neutrality, which promotes, at anode 122, the following oxidation reaction:

$$Fe^{2+}+3H_2O \rightarrow Fe(OH)_3+3H^++e^- \qquad (5)$$

An electron transfer from anode 122 to cathode 124 through conductive element 120 and thus through load C to be powered can thus be observed.

Reaction (4) thus causes the consumption of the ferric hydroxide Fe(OH)$_3$ of cathode 124. To enable a long-term operation of cell 100, it is advantageous to provide a regular inversion of the polarity of cell 100.

FIG. 9B shows cell 100 in a second operating phase. Valve 108 is closed and valve 110 is open. Further, valve 14 is open and valve 14' is closed. Previously-described reactions (1) which take place in enclosure 12 cause the releasing of H$^+$ ions which disseminate outside of device 10, into region 104 of enclosure 102, and in particular at the level of electrode 122, which then behaves as a cathode. The presence of H$^+$ ions at the level of cathode 122 promotes previously-described reduction reaction (4).

Since valve 14' is closed, device 10' releases no H$^+$ ions into region 106 of enclosure 102. Further, since valve 108 is closed and valve 110 is open, the establishment of a pH gradient between region 106 and region 104 of enclosure 102 is promoted, the pH being higher in region 106 than in region 104. Indeed, the H$^+$ ions which propagate to region 106 tend to react, for example, with OH$^-$ hydroxyl ions present in the biological solution and crossing membrane 114 to form water or with HCO$_3^-$ bicarbonate ions to form water and carbon dioxide.

The Fe$^{2+}$ ions, which form at cathode 122, are trapped in enclosure 102 and migrate to electrode 124, which then behaves as an anode. The previously-described oxidation reaction (5) is thus promoted at anode 124.

An electron transfer from anode 124 to cathode 122 can thus be observed through conductive element 120 and thus through load C to be powered.

The operating phases previously described in relation with FIGS. 9A and 9B are alternated to enable restoring the Fe(OH)$_3$ stock at the level of electrodes 122, 124.

Figure 10:
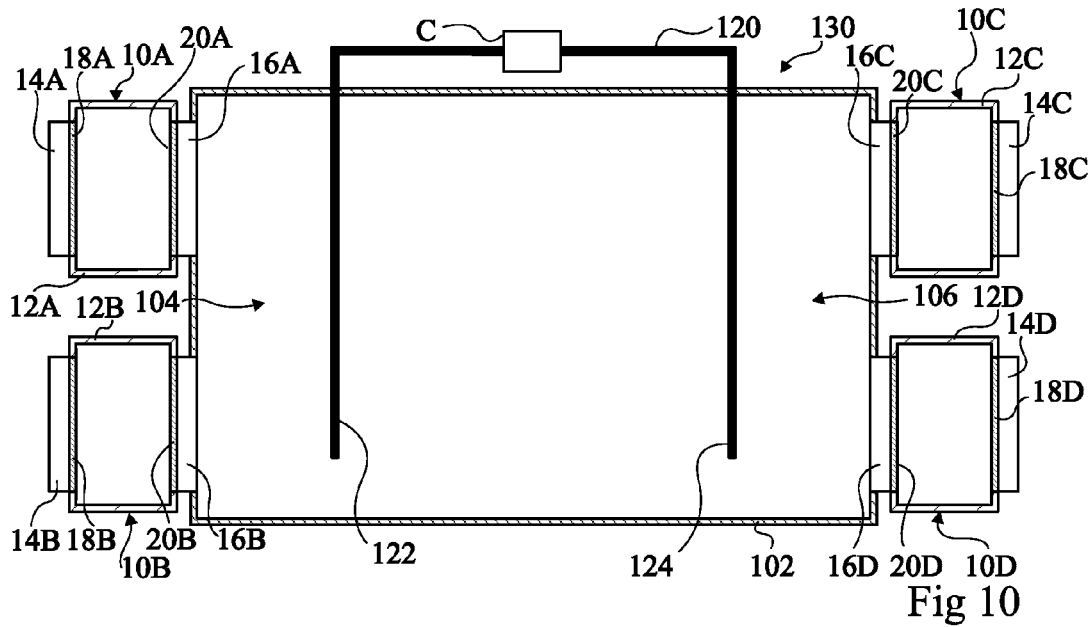
FIG. 10 shows a second embodiment of an electric cell implementing the first embodiment of the device for varying the pH according to the present invention.

FIG. 10 shows a second embodiment of a cell 130 implementing the first example of a device for varying the pH according to the invention. Cell 130 can operate without being immersed in a biological solution. As compared with cell 100, cell 130 comprises four devices for varying the pH such as described previously in relation with FIG. 1. In the following description, suffixes "A", "B", "C", and "D" are added to designate the elements respectively associated with devices 10A, 10B, 10C, and 10D for varying the pH. Valves 16A and 16B of devices 10A, 10B emerge at the level of region 104 of enclosure 102 and valves 16C and 16D of devices 10C, 10D emerge at the level of region 106 of enclosure 102.

Devices 10A and 10C are of the type enabling to decrease the pH of the solution that they contain. As an example, devices 10A and 10C enable to acidify the solution contained in the associated enclosure 12A, 12C according to previously-described reactions (1). Devices 10B and 10D are of the type enabling to increase the pH of the solution that they contain. As an example, devices 10B, 10D enable an alkalizing of the solution contained in the associated enclosure 12B, 12D according to previously-described reactions (3).

An example of operation of cell 130 is the following. In parallel with the opening cycle of valves 16A to 16D which will now be described, devices 10A to 10D are controlled so that the associated enclosures 12A to 12D contain solutions having the desired pH. During a first operating phase, valve 16A is open, valve 16B is closed, valve 16C is closed, and valve 16D is open. H$^+$ ions are then released by device 10A, the decreasing the pH at the level of electrode 122 and OH$^-$ ions are released by device 10D, thus increasing the pH at the level of electrode 124. A pH gradient is then obtained between regions 104 and 106 of enclosure 102. The presence of H$^+$ ions at the level of electrode 122 promotes previously-described reduction reaction (4) and the presence of OH$^-$ ions at the level of electrode 124 promotes previously-described oxidation reaction (5). An electron transfer from anode 124 to cathode 122 through conductive element 120 and thus through load C to be powered can thus be observed. During a second operating phase, valve 16A is closed, valve 16B is open, valve 16C is open and valve 16D is closed. H$^+$ ions are then released by device 10C, thus decreasing the pH at the level of end 124 and OH$^-$ ions are released by device 10B, thus increasing the pH at the level of electrode 122. The presence of H$^+$ ions at the level of electrode 124 promotes previously-described reduction reaction (4) and the presence of OH$^-$ ions at the level of electrode 122 promotes previously-described oxidation reaction (5). An electron transfer from anode 122 to cathode 124 through conductive element 120 and thus through load C to be powered can thus be observed.

In the previously-described cell examples, it is possible to use, instead of ferric hydroxyl, several sorts of electrodes, provided that their potential depends on the pH. The electrode potential being imposed by the electronic exchange between the two forms of a redox pair, it is possible to envisage different electrode structures: the two forms may be soluble, one form may be soluble and the other insoluble, and finally, both forms may be insoluble. In this last case, it may be advantageous to use electrodes formed of an electro-active polymer obtained, for example, from a condensation of phenols and thiols. An example of a polymer having a redox capacity is described in document Ion Exchange, Friedrich Helfferich, 1962 McGraw-Hill Book Company, Chapter 12: Electron Exchangers and Redox Ion Exchangers, pages 551 to 568.

Figure 11:
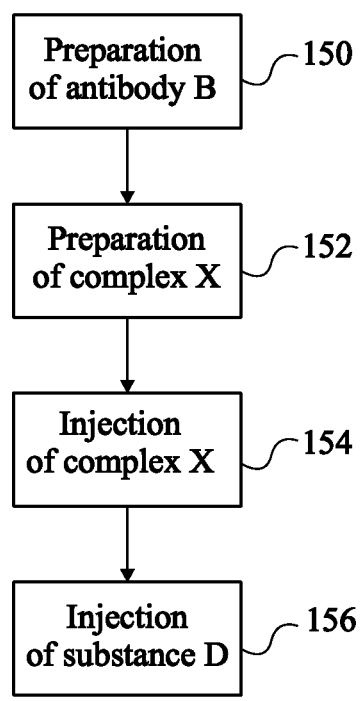
FIG. 11 illustrates a processing method according to the present invention.

FIG. 11 illustrates the steps of an example of a targeted enzyme therapy method. An example of a targeted enzyme therapy method is described in document "Lysosomal Enzyme Delivery by ICAM-1-Targeted Nanocarriers Bypassing Glycosylation- and Clathrin-Dependent Endocytosis" by Sylvia Muro, Edward H. Schuchman, and Vladimir R. Muzykantov (Molecular Therapy vol. 13, n° 1, January 2006, pages 135 to 140).

At step 150, a monoclonal antibody B recognizing an antigen A of the target cell is determined. As an example, antigen A corresponds to the carcinoembryonic antigen or CEA, the prostate specific antigen (PSA), or the prostate specific membrane antigen (PSMA). An antibody B adapted to the PSA antigen is, for example, the antibody marketed by Cytrogen Corporation under trade name Prostascint (Capromab Pendetide).

At step 152, a complex X combining monoclonal antibody B and an enzyme G is formed. Enzyme G is capable of promoting a reaction implementing a substance D. Complex X is such that the affinity of antibody B with antigen A remains strong and that the activity of enzyme G on substance D also remains strong. Substance D is, for example, L-glucose and enzyme G corresponds to an L-glucose oxidase enzyme, for example, D-threo-aldose 1-dehydrogenase. Such an enzyme has the advantage of being inactive on D-glucose.

According to another example, substance D is mannitol ($C_6H_8(OH)_6$) and enzyme G corresponds to a mannitol oxidase enzyme.

At step 154, complex X is injected into the patient's body. The injection of complex X is, for example, intravenous. Complex X then tends to fix on antigen A via antibody B. It is then expected for complex X flowing in the patient's body to be eliminated.

At step 156, substance D is injected into the patient's body. The injection of substance D is, for example, intravenous. In the case where enzyme G is an L-glucose oxidase, L-glucose is injected into the patient's body. L-glucose then freely diffuses into the organism. L-glucose being harmless for the human body, the L-glucose concentration may be high (for example on the order of the blood glucose concentration, that is, several millimoles per liter). In the case where enzyme G is a mannitol oxidase, mannitol, for example, the D stereoisomer of mannitol, is injected into the patient's body.

In the case of an L-glucose injection, since human cells are not capable of metabolizing L-glucose, only enzymes G of complexes X will promote the previously-described reactions (2), causing, the production of $H^+$ ions from the L-glucose and, accordingly, a local pH decrease. Such a local pH decrease may provide a direct therapeutic effect, causing the death of the target cell, or may cause an inflammatory response causing the death of the target cell.

In the case of a mannitol injection, enzymes G promotes the reaction in which mannitol reacts with dioxygen to provide mannose ($C_6H_7O(OH)_5$) and hydrogen peroxide, or perhydrol ($H_2O_2$), according to the following reaction:

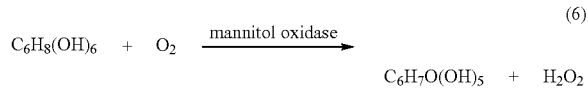

(6)

The local production of hydrogen peroxide may provide a direct therapeutic effect, causing the death of the target cell, or may cause an inflammatory response causing the death of the target cell.

An aspect of the present invention thus provides a therapeutic method comprising the steps of forming a complex comprising an antibody of an antigen of a target cell and an enzyme capable of promoting a reaction which produces a second substance from a first substance, the second substance being noxious for the target cell; introducing the complex into the patient's body, whereby the antibody of the complex fixes onto the target cell; and introducing the first substance into the patient's body, whereby the enzyme of the complex promotes the production of the second substance at the target cell level.

According to an embodiment, the first substance is L-glucose, the enzyme is the L-glucose oxidase enzyme, and the second substance is the $H^+$ ion.

According to an embodiment, the first substance is mannitol, the enzyme is the mannitol oxidase enzyme, and the second substance is hydrogen peroxide.

According to an embodiment, the antigen is an antigen from the group comprising the carcinoembryonic enzyme, the prostate specific antigen or the prostate specific membrane antigen.

Of course, the present invention is likely to have various alterations and modifications which will occur to those skilled in the art. In particular, the alternative embodiment of the expansion chamber of the osmotic motor described in relation with FIGS. 6A and 6B may be applied to the osmotic motor described in relation with FIGS. 4A to 4D.

The invention claimed is:

1. A cell (100; 130) for powering a load (C), said cell comprising:
a first enclosure (102) containing first and second electrodes (122, 124), the first and second electrodes comprising a material of a redox pair and potentials of the first and second electrodes depending on pH, a reduction or oxidation reaction being likely to occur with the material of the first and of the second electrode according to the pH;
a first device (10, 10'; 10A, 10B, 10C, 10D) for varying the pH of a solvent in which a substance is dissolved, comprising a second enclosure (12), content of the second enclosure being in contact with the content of the first enclosure via an enclosure wall permeable to the solvent and to the substance, the second enclosure containing enzymes capable of transforming the substance to release hydrogen ions or hydroxyl ions, the enclosure wall being non-permeable to enzymes, the first device being capable of bringing the pH at the level of the first electrode within a first given pH range promoting one of the reduction or oxidation reactions; and
means (108, 110; 10A, 10B, 10C, 10D) for bringing the pH at the level of the second electrode within a second given pH range different from the first range promoting the other one of the reduction or oxidation reactions.

2. The cell of claim 1, wherein the cell is intended to be arranged in contact with the solvent, said means (108, 110) corresponding to a valve likely to have the content of the first enclosure (102) communicate with the solvent at the level of the second electrode (122, 124).

3. The cell of claim 1, wherein said means (10A, 10B, 10C, 10D) are a second device for varying the pH having the same structure as the first device.

4. The cell of claim 3, wherein the first device (10; 10A, 10B) comprises a valve (14), said enclosure wall being between said valve and said second enclosure.

5. The cell of claim 3, comprising third and fourth devices for varying the pH having the same structure as the first device, the first device (10A) being capable of bringing the pH at the level of the first electrode (22) within the first given pH range promoting said one of the reduction or oxidation reactions, the second device (10D) being capable of bringing the pH at the level of the second electrode (124) within the second given pH range promoting the other one of the reduction or oxidation reactions, the third device (10C) being capable of bringing the pH at the level of the second electrode within the first given pH range promoting said one of the reduction or oxidation reactions, the fourth device (10B) being capable of bringing the pH at the level of the first electrode within the second given pH range promoting the other one of the reduction or oxidation reactions.

6. The cell of claim 1, wherein the first electrode (122) and/or the second electrode (124) comprises ferric hydroxide.

7. The cell of claim 1, wherein the first electrode (122) and/or the second electrode (124) comprises an electro-active polymer.

8. The cell of claim 1, wherein the substance is D-glucose and wherein the enzymes are glucose oxidase enzymes capable of causing the release of hydrogen ions by oxidation of the D-glucose.

9. The cell of claim 1, wherein the substance is L-glucose and wherein the enzymes are L-fucose dehydrogenase enzymes capable of causing the release of hydrogen ions by oxidation of the L-glucose.

10. The cell of claim 1, wherein the substance is urea and wherein the enzymes are urease enzymes capable of causing the release of hydroxyl ions by ureal degradation.

11. A method comprising the following steps:
providing the cell of claim 1;
having the first device (10A) bring the pH at the level of the first electrode (122) within said first given pH range promoting said one of the reduction or oxidation reactions with the material of the first electrode; and
having said means bring the pH at the level of the second electrode (124) within said second given pH range promoting the other one of the reduction or oxidation reactions with the material of the second electrode.

12. The method of claim 11 for operating the cell of claim 3, wherein step (b) comprises having said second device (10; 10D) bring the pH at the level of the second electrode (124) within said second given pH range.

13. The method of claim 12 for operating the cell of claim 4, further comprising the following steps implemented after steps (a) and (b):
(c) having said third device (10C) bring the pH at the level of the second electrode (124) within said first given pH range promoting said one of the reduction or oxidation reactions with the material of the second electrode;
(d) having said fourth device (10B) bring the pH at the level of the first electrode (122) within said second given pH range promoting the said other one of the reduction or oxidation reactions with the material of the first electrode.

14. The method of claim 11, wherein the first electrode (122) and/or the second electrode (124) comprises ferric hydroxide.

15. The method of claim 11, wherein the first electrode (122) and/or the second electrode (124) comprises an electro-active polymer.

16. The method of claim 11, wherein the substance is D-glucose and wherein the enzymes are glucose oxidase enzymes capable of causing the release of hydrogen ions by oxidation of the D-glucose.

17. The method of claim 11, wherein the substance is L-glucose and wherein the enzymes are L-fucose dehydrogenase enzymes capable of causing the release of hydrogen ions by oxidation of the L-glucose.

18. The method of claim 11, wherein the substance is urea and wherein the enzymes are urease enzymes capable of causing the release of hydroxyl ions by ureal degradation.

* * * * *

UNITED STATES PATENT AND TRADEMARK OFFICE
CERTIFICATE OF CORRECTION

PATENT NO. : 9,127,651 B2
APPLICATION NO. : 12/517395
DATED : September 8, 2015
INVENTOR(S) : Philippe Cinquin et al.

It is certified that error appears in the above-identified patent and that said Letters Patent is hereby corrected as shown below:

Title page, item (73) Assignee, should read as follows:

UNIVERSITE JOSEPH FOURIER
Grenoble Cedex 9, France and

INSTITUT NATIONAL DES SCIENCES APPLIQUEES DE TOULOUSE
Toulouse Cedex 4, France

Signed and Sealed this
Fifth Day of July, 2016

Michelle K. Lee
*Director of the United States Patent and Trademark Office*